US00RE36476E

United States Patent [19]

Khouri et al.

[11] E Patent Number: Re. 36,476

[45] Reissued Date of Patent: Dec. 28, 1999

[54] METHOD OF INHIBITING MICROVASCULAR THROMBOSIS

[75] Inventors: Roger K. Khouri; Tze-Chein Wun, both of St. Louis, Mo.

[73] Assignee: Washington University, St. Louis, Mo.

[21] Appl. No.: 08/599,398

[22] Filed: Jan. 3, 1996

Related U.S. Patent Documents

Reissue of:

[64] Patent No.: 5,276,015
Issued: Jan. 4, 1994
Appl. No.: 07/853,457
Filed: Mar. 18, 1992

[51] Int. Cl.[6] ..... C12N 9/00; C12N 7/00; A61K 38/16

[52] U.S. Cl. ..... 514/12; 514/21

[58] Field of Search ..... 514/12, 21

[56] References Cited

U.S. PATENT DOCUMENTS 4,966,852 10/1990 Wun et al. ..... 435/320.1

OTHER PUBLICATIONS

Wun, J. Biol. Chem, vol. 263, pp. 6001–6004, 1988.

Cooley et al., Microsurgery, vol. 6, pp. 46–48, 1985.

Rapaport, Blood, vol. 73, pp. 359–365, 1989.

Broze et al. Biochemistry, vol. 29, pp. 7539–7546, 1990.

Dorland's Illustrated Medical Dictionary, 27$^{th}$ Edition, W. B. Saunders Company, p. 1038, 1988.

Cooley et al., Microsurgery, vol. 12, pp. 281–287, 1991.

Haskel et al., Circulation, vol. 84, pp. 821–827, 1991.

Day et al., Blood, vol. 76(8), pp. 1538–1545, 1990.

Salemark, Microsurgery, vol. 12, pp. 308–311, 1991.

*Primary Examiner*—Chhaya D. Sayala
*Attorney, Agent, or Firm*—Banner & Witcoff

[57] ABSTRACT

A method for reducing the thrombogenicity of microvascular anastomoses in a warm blooded mammal comprising administering to said mammal at the site of said microvascular anastomoses contemporaneously with microvascular reconstruction of a small but inhibitory effective amount of TFPI.

36 Claims, 6 Drawing Sheets

METHOD OF INHIBITING MICROVASCULAR THROMBOSIS

Matter enclosed in heavy brackets [ ] appears in the original patent but forms no part of this reissue specification; matter printed in italics indicates the additions made by reissue.

BACKGROUND OF THE INVENTION

This invention relates to a novel method for inhibiting microvascular thrombosis and, more particularly, to a method for reducing the thrombogenicity of microvascular anastomoses during microvascular reconstruction by the topical administration of a blood coagulation inhibitor known as lipoprotein-associated coagulation inhibitor (LACI) and alternatively as tissue factor pathway inhibitor (TFPI).

Thrombosis of microvascular anastomoses, particularly in cases of extremity trauma in free flap reconstructions, is a significant problem for the reconstructive surgeon. A recent survey by Salemark, Microsurgery 12, 308–311 (1991), revealed that many centers routinely make use of systemic anticoagulation for replants and free flap transfers. However, the risk for generalized hemorrhage [Leung, Hand 12, 25–32 (1980); Hirsh, Semin. Thromb. Hemostas. 12, 21–32 (1980)], with compounding risks from blood transfusion products, leaves open the question of benefit from massive systemic circulatory alteration merely to preserve flow in a small vessel supplying blood to non-vital tissue.

The concept of site-specific action by an antithrombotic agent, administered through simple topical application was proposed by Cooley and Gould, Microsurgery 12, 281–287 (1991). Since those vessels which are prone to thrombosis are exposed during the reconstructive effort, with ready access to the lumenal surface during the anastomotic repair, an agent could be applied through the course of normal vessel irrigation, potentially achieving a highly localized effect through surface binding to the thrombogenic site(s). In fact, Cooley et al. have described one possible agent, a peptide based on the platelet-binding and fibrin-polymerizing region of fibrinogen, and have shown its ability to reduce the occurrence of thrombotic occlusion in a rat model [6th Ann. Meeting, Amer. Soc. Reconstructive Microsurgery, Toronto, Canada. Sep. 21–23, 1990].

Thrombosis caused by vascular injury is at least partially if not predominantly initiated through the tissue-factor-mediated pathway of coagulation.

Plasma contains a multivalent Kunitz-type inhibitor of coagulation, referred to herein as tissue factor pathway inhibitor (TFPI). This name has been accepted by the International Society on Thrombosis and Hemostasis, Jun. 30, 1991, Amsterdam. TFPI was first purified from a human hepatoma cell, Hep G2, as described by Broze and Miletich, Proc. Natl. Acad. Sci. USA 84, 1886–1890 (1987), and subsequently from human plasma as reported by Novotny et al., J. Biol. Chem. 264, 18832–18837 (1989); Chang liver and SK hepatoma cells as disclosed by Wun et al., J. Biol. Chem. 265, 16096–16101 (1990). TFPI cDNA have been isolated from placental and endothelial cDNA libraries as described by Wun et al., J. Biol. Chem. 263, 6001–6004 (1988); Girard et al., Thromb. Res. 55, 37–50 (1989). The primary amino acid sequence of TFPI, deduced from the cDNA sequence, shows that TFPI contains a highly negatively charged amino-terminus, three tandem Kunitz-type inhibitory domains, and a highly positively charged carboxyl terminus. The first Kunitz-domain of TFPI is needed for the inhibition of the factor $VII_a$/tissue factor complex and the second Kunitz-domain of TFPI is responsible for the inhibition of factor $X_a$ according to Girard et al., Nature 328, 518–520 (1989), while the function of the third Kunitz-domain remains unknown. See also copending application Ser. No. 07/301,779, filed Jan. 26, 1989, now U.S. Pat. No. 5,106,833. TFPI is believed to function in vivo to limit the initiation of coagulation by forming an inert, quaternary factor $X_a$: TFPI: factor $VII_a$: tissue factor complex. Further background information on TFPI can be had by reference to the recent reviews by Rapaport, Blood 73, 359–365 (1989); Broze et al., Biochemistry 29, 7539–7546 (1990).

Recombinant TFPI has been expressed as a glycosylated protein using mammalian cell hosts including mouse C127 cells as disclosed by Day et al., Blood 76, 1538–1545 (1990), baby hamster kidney cells as reported by Pedersen et al., J. Biol. Chem. 265, 16786–16793 (1990), Chinese hamster ovary cells and human SK hepatoma cells. The C127 TFPI has been used in animal studies and shown to be effective in the inhibition of tissue factor-induced intravascular coagulation in rabbits according to Day et al., supra, and in the prevention of arterial reocclusion after thrombolysis in dogs as described by Haskel et al., Circulation 84, 821–827 (1991).

Recombinant TFPI also has been expressed as a non-glycosylated protein using E. coli host cells and obtaining a highly active TFPI by in vitro folding of the protein as described in co-pending application of Judy A. Diaz-Collier, Mark E. Gustafson and Tze-Chein Wun, on "Method of Producing Tissue Factor Pathway Inhibitor", Ser. No. 07/844,297, filed Mar. 22, 1992, now U.S. Pat. No. 5,112,091, the disclosure of which is incorporated by reference herein.

The cloning of the TFPI cDNA which encodes the 276 amino acid residue protein of TFPI is further described in Wun et al., U.S. Pat. No. 4,966,852, the disclosure of which is incorporated by reference herein.

BRIEF DESCRIPTION OF THE INVENTION

In accordance with the present invention a novel method is provided for inhibiting microvascular thrombosis. The method comprises topically administering to a warm blooded mammal at the site of microvascular anastomoses contemporaneously with microvascular reconstruction of a small, but effective amount of TFPI sufficient to reduce the thrombogenicity of microvascular anastomoses.

The invention is illustrated herein by topical application of the TFPI to a rabbit ear artery model of crush/avulsion injury subjected to microvascular repair. In this illustrative topical application of TFPI, traumatized arteries treated through lumenal irrigation with normal saline vehicle (controls) achieved patency rates of 8% and 0% at 1 and 7 days postoperatively (p.o.), respectively. Heparin irrigation (10 units/ml) resulted in patencies of 40% at both evaluation times. In contrast, TFPI at a dose of 20 $\mu$g/ml (0.2 ml total volume; 10-minute exposure) yielded a 91% patency rate at 1 day, and 73% at 7 days p.o. ($p<0.0005$ vs. controls). Systemic anticoagulation effect was checked with peripheral blood prothrombin time (PT) and activated partial thromboplastin time (APTT). These values were not altered after topical treatment with TFPI. Scanning electron microscopy revealed dramatically inhibited thrombogenesis upon the injured surfaces of TFPI-treated vessels. These results support the effectiveness of TFPI used as a topically-applied antithrombotic agent for the prevention of thrombosis in clinical microvascular surgery.

It will be appreciated that the method of the invention is useful for other warm blooded mammals, e.g. humans, in a analogous manner. It is expressly adapted for microvascular reconstruction such as by free flap transfer or replantation surgery.

As defined herein, TFPI can be either glycosylated or non-glycosylated.

DETAILED DESCRIPTION OF THE INVENTION

Figure 1:
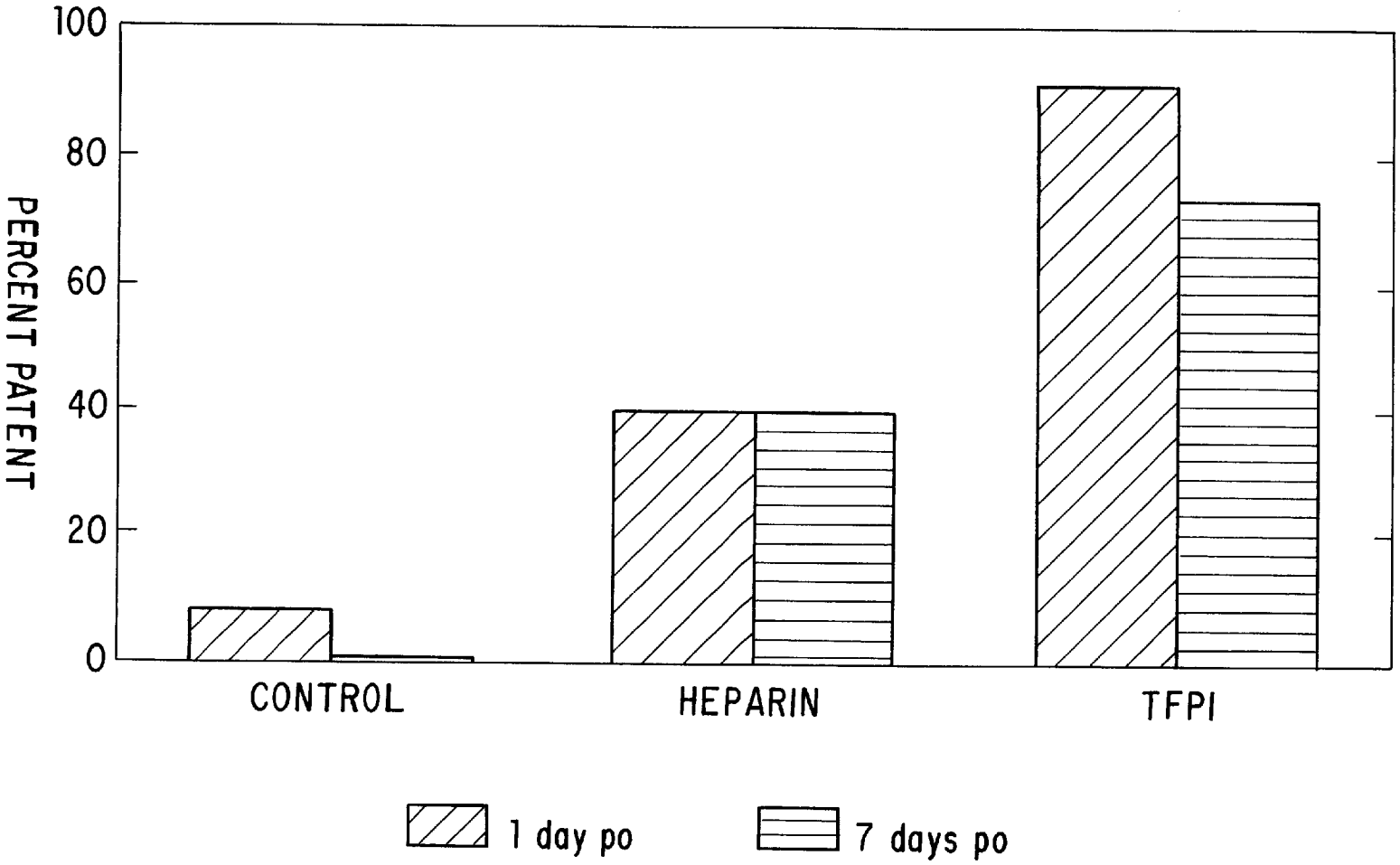

While the specification concludes with claims particularly pointing out and distinctly claiming the subject matter which is regarded as forming the present invention, it is believed that the invention will be better understood from the following detailed description of preferred embodiments taken in conjunction with the accompanying drawings in which:

FIG. 1 is a bar graph that shows the patency rates achieved at 1 and 7 days postoperatively, for each of three treatment groups, in which topical administration of TFPI during microvascular repair of a vascular trauma in a rabbit ear model is compared with similar administration of heparin or the control vehicle (normal saline) without either TFPI or heparin.

Figure 2A:
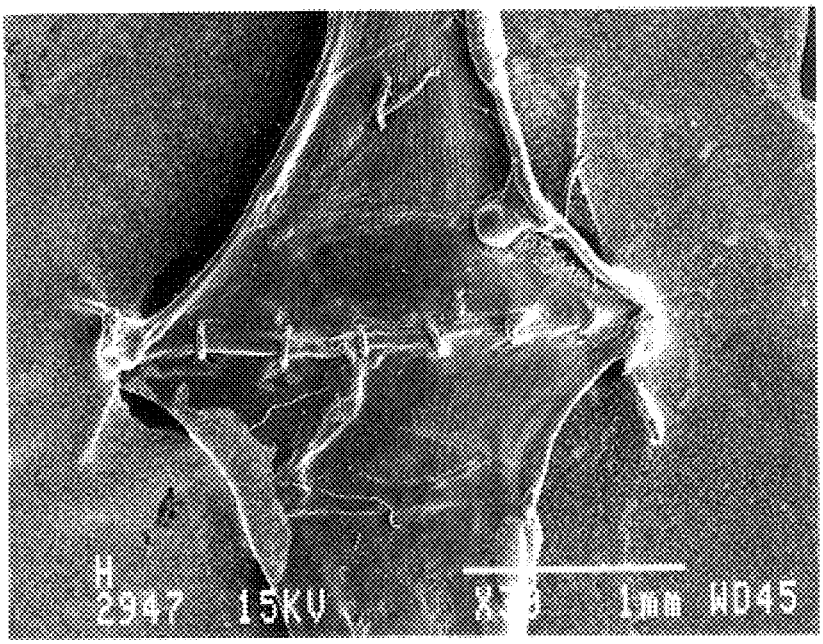
Figure 2B:
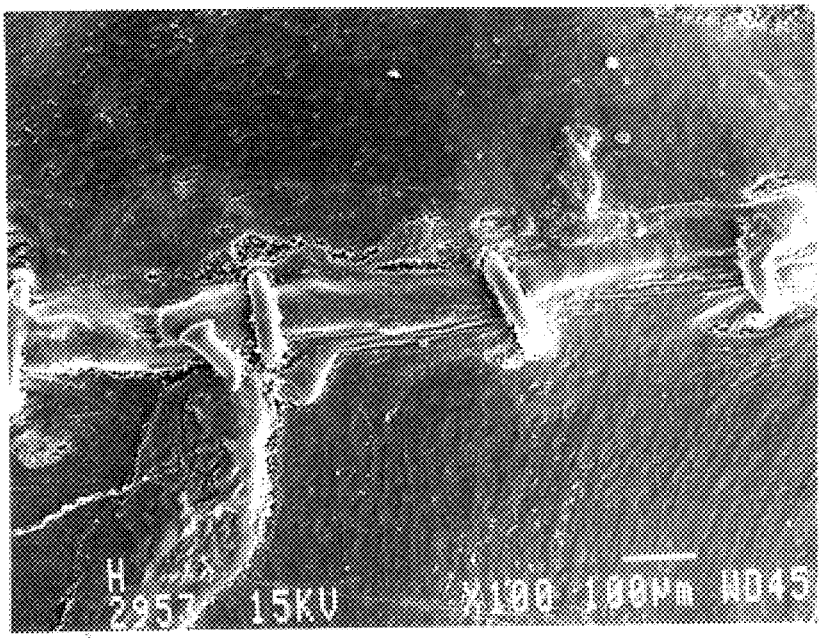
Figure 2C:
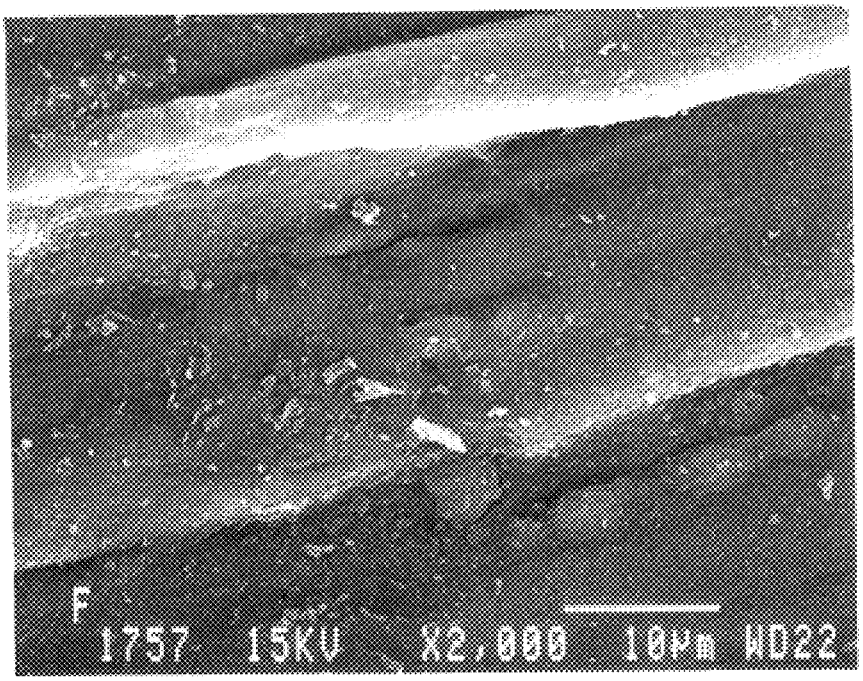

FIG. 2, in 3 parts, namely FIGS. 2A, 2B and 2C, shows the scanning electron micrographs at several magnifications of the lumenal surfaces of vessels one hour after reflow, following microvascular repair and topical administration of TFPI as in FIG. 1. FIG. 2A=30X; FIG. 2B=100X; FIG. 2C=2000X.

Figure 3A:
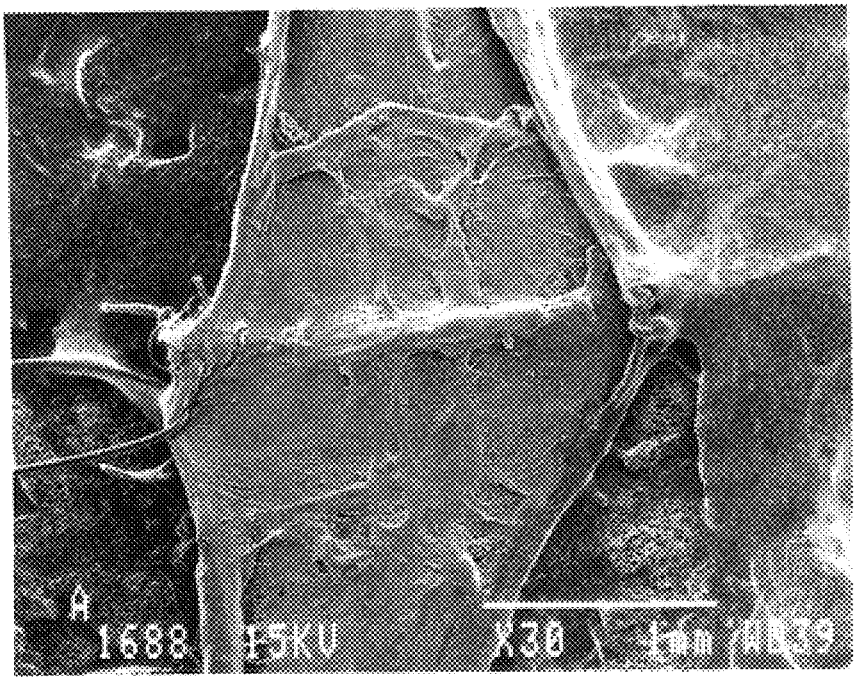
Figure 3B:
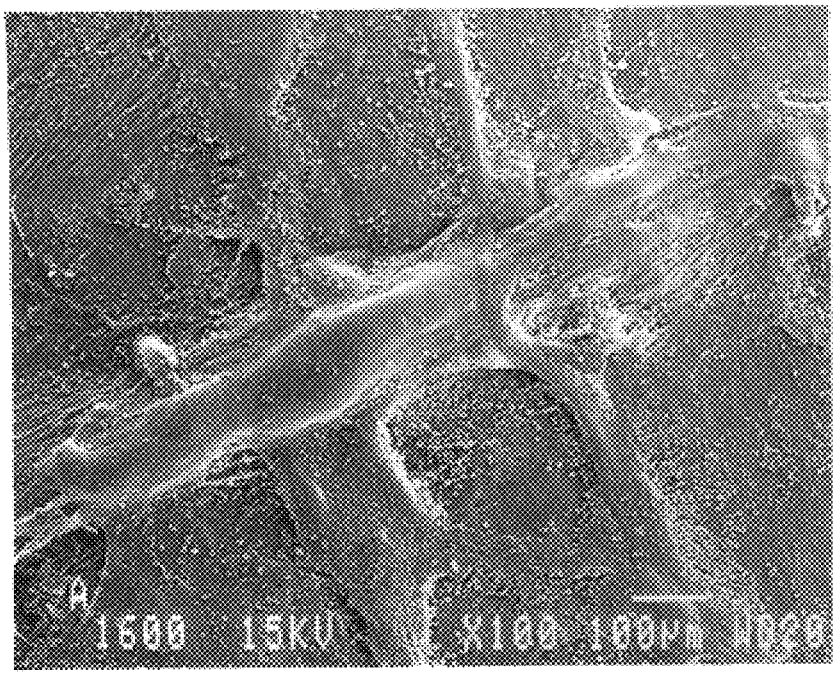
Figure 3C:
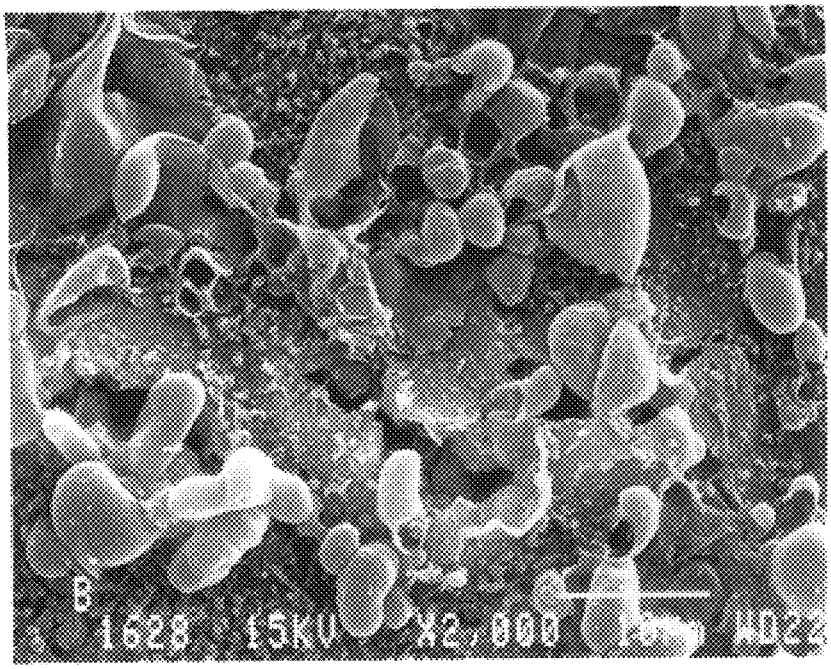

FIG. 3, in 3 parts, namely FIGS. 3A, 3B and 3C, shows scanning electron micrographs at several magnifications of the lumenal surfaces one hour after reflow, following microvascular repair and topical administration of heparin as in FIG. 1. FIG. 3A=30X; FIG. 3B=100X; FIG. 3C=2000X.

Figure 4A:
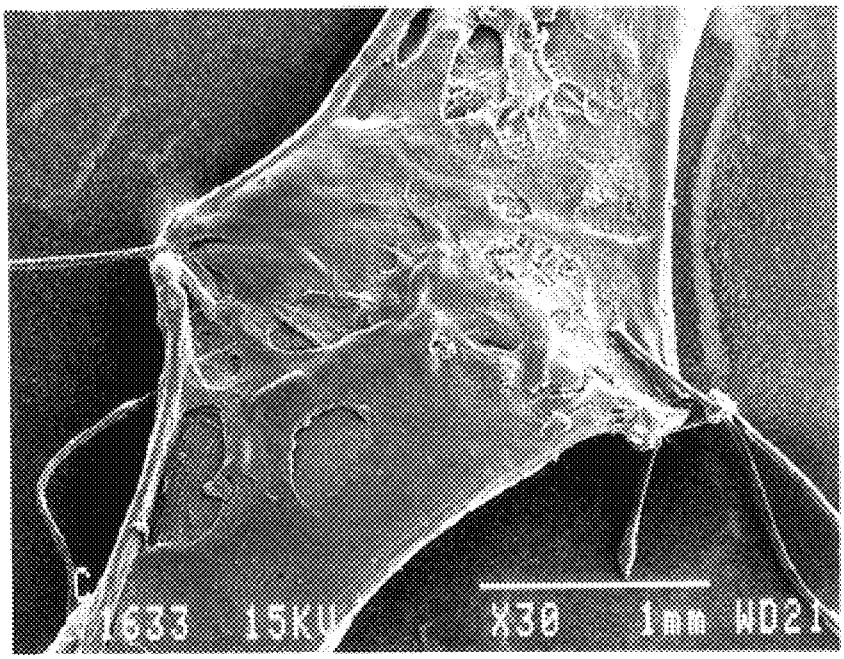
Figure 4B:
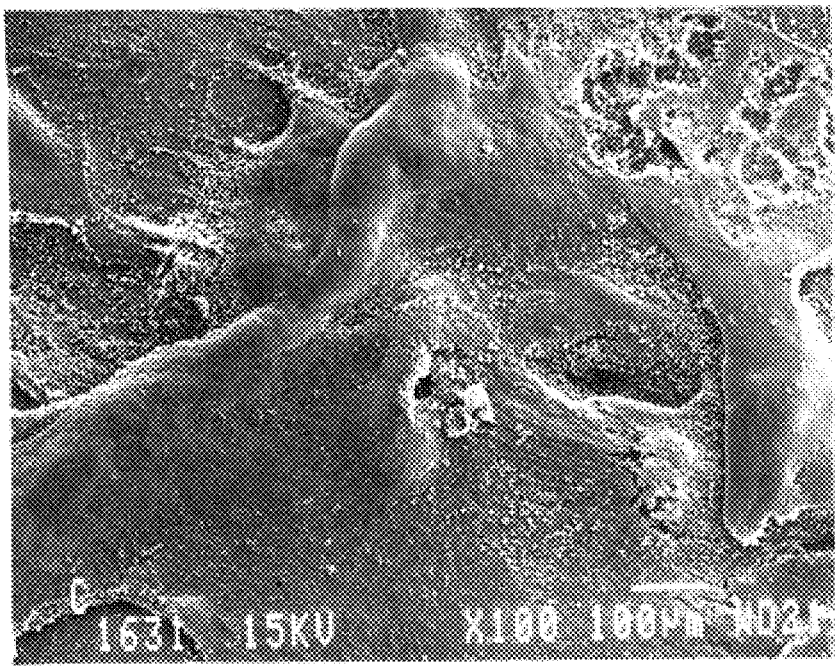
Figure 4C:
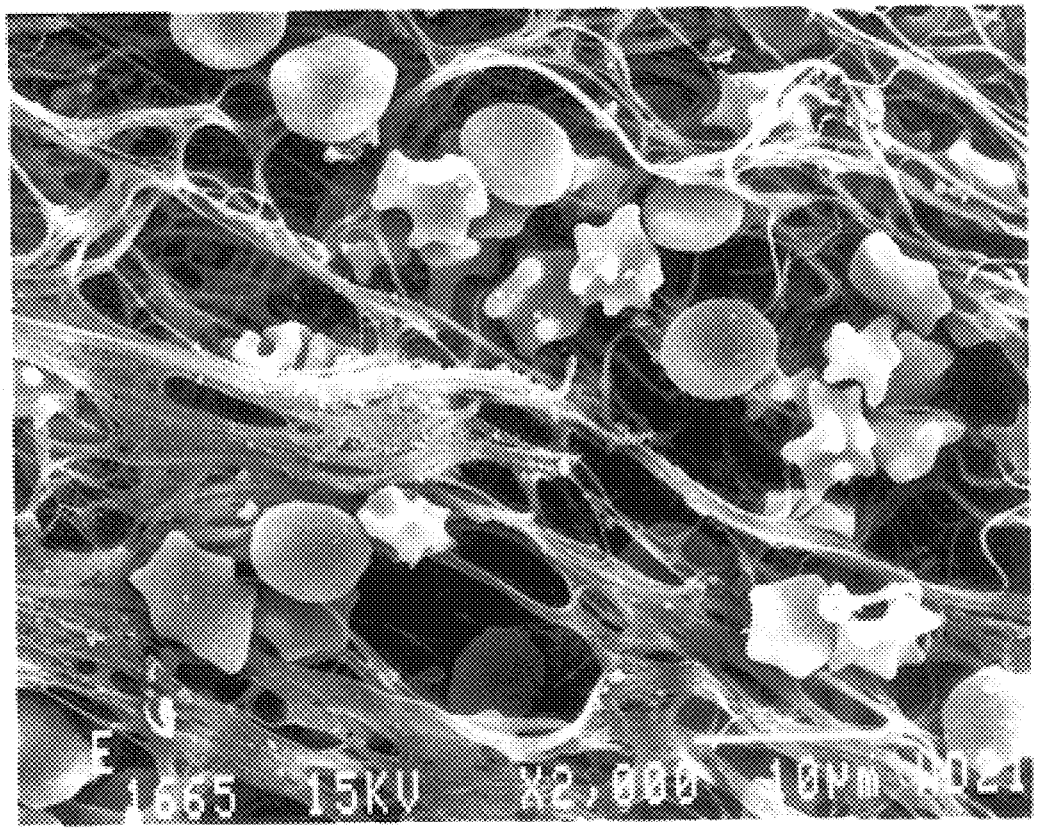

FIG. 4, in 3 parts, namely FIGS. 4A, 4B and 4C, shows scanning electron micrographs at several magnifications of the lumenal surfaces one hour after reflow, following microvascular repair and topical administration of the control vehicle without either TFPI or heparin as in FIG. 1. FIG. 4A=30X; FIG. 4B=100X; FIG. 4C=2000X.

In order to illustrate the invention in greater detail, the following illustrative microsurgical repair of vascular trauma accompanied with administration of TFPI was carried out. It will be appreciated, however, that the invention is not limited to this exemplary work or to the specific details set forth in these examples.

EXAMPLES

Materials and Methods

The NIH guidelines for the care and use of laboratory animals were followed throughout. New Zealand White rabbits (3–5 lbs) were anesthetized with intramuscular injection of ketamine (100 mg) and xylaaine (20 mg). Under sterile conditions, the central ear artery was exposed over a length of 20 mm. A modification of the crush-avulsion injury of Cooley and Hansen, Microsurgery 6, 46 48 (1985), was created as follows. Two Webster needleholders were clamped firmly upon the artery 2 mm from each other, then moved apart in proximal-distal directions, traumatically severing the artery. Temporary microvascular clamps were applied beyond the Webster crush sites, and the lumen was flushed with normal saline. The torn ends of the artery were minimally trimmed, preserving essentially the entire length of traumatized artery. An end-to-end anastomosis was next performed using 8–10 stitches of 10-0 nylon suture. Before tying the last stitch, 0.2 ml of a test solution was irrigated across the anastomosis and injured lumen, filling the vessel with the fluid. It was left in place for 10 minutes, then washed out with normal saline. One of three solutions was used per vessel on a blinded, randomized basis: TFPI at a concentration of 20 $\mu$g/ml in normal saline, heparin (10 units/ml) in normal saline, or normal saline (the control vehicle).

The TFPI used in these Examples was obtained through recombinant DNA clones expressed in E. coli It is a 277 amino acid protein consisting of the 276 residue sequence described by Wun et al., J. Biol. Chem. 263, 6001–6004 (1988), and in U.S. Pat. No. 4,966,852, with an additional Alanine residue inserted at the N-terminus as further described in the aforesaid copending application of Diaz-Collier, Gustafson and Wun, Ser. No. 07/844,297, filed Mar. 22, 1992, now U.S. Pat. No. 5,212,091. It is >95% homogeneous.

Upon completion of the repair and irrigation of the lumen as described above, the temporary clamps were released. In 34 arteries (from 17 rabbits), the patency was followed for 1 hour, then the wound was closed Re-anesthetization was induced at 1 and 7 days post-operatively for re-evaluation of patency.

In a separate series, 9 arteries (from 5 rabbits), were divided into 3 groups of 3 vessels each; TFPI, heparin or vehicle was administered to each as described above. The injured and repaired vessels were harvested after 1 hour of flow, fixed in buffered glutaraldehyde, and prepared for examination of the lumenal surfaces with a scanning electron microscope. Blood was drawn from a femoral vein branch before arterial injury and again one hour after reflow (before vessel harvest). Prothrombin (PT) and activated partial thromboplastin (APTT) times were determined on plasma samples using a standard, commercially available fibrometer.

Results

Patency rates for all groups are shown in FIG. 1. All vessels that were patent at 1 day had shown clear patency at 1 hour of reflow. Vessels found thrombosed at 1 day were still thrombosed at 7 days, for all groups. The patency rates for the control (vehicle-treated) arteries were 8% (1/13) at 1-day and 0% (0/13 at 7 days postoperatively. Heparin-treated vessels achieved 40% (4/10) patency at both 1 and 7 days, with a significant improvement noted at 7 days ($p < 0.025$; Fisher exact test). TFPI treatment resulted in 91% (10/11) and 73% (8/11) patency rates at 1 and 7 days, significantly better than controls for both time periods ($p < 0.0005$). The TFPI-treated vessels had a significantly higher patency than heparin-treated vessels at 1 day ($p < 0.02$), but not at 7 days ($p > 0.1$).

Peripheral blood PT and APTT values for TFPI-treated rabbits were within the normal range (6–8.5 sec. for PT; 14–18 sec. for APTT). The times for each animal showed no differences between pre- and post-treatment values.

Scanning electron microscopy at 15 KV of patent specimens harvested after 1 hour of flow showed at 30× magnification a suture line obscured by thrombus in control (FIG. 4A) and heparin-treated (FIG. 3A) vessels. In contrast, the suture line and surrounding vessel lumen was virtually clear of any sizable thrombotic accumulation in TFPI-treated vessels (FIG. 2A). At higher magnification (100× and 2000×), the controls displayed a mixed thrombus of fibrin strands and platelet aggregates. Heparin-treated vessels had dramatically less fibrin strand formation, with most of the thrombus composed of platelet aggregates and entrapped red blood cells (FIGS. 3B and C). TFPI-treated vessels showed very few organized thrombotic elements, leaving what appeared to be a surface relatively inert to thrombogenesis (FIGS. 2B and C).

Relative to the problems encountered with large vessel, cerebral and coronary thrombosis, reconstructive microvascular surgery has the great advantage of easy and often necessary surgical access to the vessels that are most prone to thrombosis. During the microvascular repair, the surgeon is able to achieve direct exposure of the thrombogenic surface. The standard treatment for injured vessels has been to identify all traumatized portions, to resect and replace (with vein grafts) those considered too severely injured, and to administer systemic antithrombotic agents (heparin, aspirin, dipyridamole, and/or dextran most frequently) to prevent the occurrence of subsequent thrombosis. Several problems may exist, not all of which may be known to the surgeon: an apparently normal vessel surface may in fact have a significant thrombogenic capacity, due to endothelial denudation, fine medial tears, or possibly an activated coagulation pathway on the surface of an otherwise uninjured vessel; the extent of vessel injury may be beyond direct visibility to the surgeon, even with the aid of a microscope; vein grafts may be limited in availability or the selection may be less than ideal; the traumatic incident or an unsuspected systemic coagulopathy may augment the probability for localized or generalized hemorrhage, respectively. For these reasons, the development of an efficacious antithrombotic agent applied through intra-operative topical irrigation in accordance with the present invention is useful and very practical.

Heparin has been shown to have a high affinity for endothelium in vivo. [Hiebert and Jaques, Thrombosis Res. 8, 195–204 (1976); Hiebert and Jaques, Artery 2, 26–37 (1976); Mahadoo et al., Thrombosis Res. 12, 79–90 (1977)]. A significant improvement in microvascular patency with topical heparin compared with unheparinized solutions has been shown experimentally. Reichel et al., J. Hand Suro. 13A, 33–36 (1988), using a rat crushed artery model of thrombosis, demonstrated that heparin, urokinase and other agents moderately enhanced patencies (up to 55%, compared to a control level of 10%) after topical administration only. A more dramatic improvement was noted by Cooley et al. using a 21-residue peptide homologue to the carboxy-terminus of the fibrinogen gamma chain (83% patent, compared with 17% for controls). [6th Ann. Meeting, Amer. Soc. Reconstructive Microsurgery, Toronto, Canada, Sep. 21–23 (1990)]. In accordance with the present invention, comparably high levels of success using a substantially different agent, TFPI.

Recent studies with TFPI using in vitro assays have shown that it forms a complex with tissue factor, and Factors VIIA and Xa, rendering these key clotting cascade enzymes ineffective. [Broze et al., Blood 71, 335 (1988)]. In accordance with the present invention, topical application of TFPI to a traumatized vessel surface may allow it to complex with these enzymes which have been activated through the vascular injury. Following blood flow reestablishment, the capacity of the extrinsic pathway of coagulation at this site is substantially reduced. Since TFPI can be applied locally and in minute quantities, systemic effects are virtually non-existent, as was shown by the foregoing results.

Topical administration of the TFPI can be carried out by conventional methods of administration of topically effective drugs which are well-known to persons skilled in the art. For example, the TFPI can be administered topically in the conventional manner whereby heparin is thus administered as a topical agent during microsurgery. See, e.g., Cooley and Gould, Microsurgerv 12, 281–287 (1991). For conventional methods of topical administration reference can also be had to the numerous texts and treatises in the field of drug administration, e.g., Remington's Pharmaceutical Sciences, Ed. Arthur Osol, 16th ed., 1980, Mack Publishing Co., Easton, PA. Preferably, the TFPI is carried in a physiologically acceptable vehicle or control such as normal saline or buffered saline such as with phosphate buffered saline or other such pharmaceutically acceptable buffers, e.g., HEPES. It can also be administered in a powder, salve or ointment form in conventional vehicles. The amount of TFPI administered to the site of the vascular trauma can be a very small amount, depending in part, on the degree and extent of the trauma. Doses of TFPI of from about 1 $\mu$g/ml to about 100 $\mu$g/ml applied in a volume of about 0.01 to about 1 ml volume over an exposure period of 1 to several minutes are suitable.

Various other examples will be apparent to the person skilled in the art after reading the present disclosure without departing from the spirit and scope of the invention. It will be understood that all such other examples are included within the scope of the appended claims.

What is claimed is:

1. A method for reducing the thrombogenicity of microvascular anastomoses in a warm blooded mammal comprising administering topically to said mammal at the site of said microvascular anastomoses contemporaneously with microvascular reconstruction a small but inhibitory effective amount of from about 1 $\mu$g/ml to about 100 $\mu$g/ml applied in a volume of about 0.01 to about 1 ml volume of TFPI.

2. The method of claim 1 in which the TFPI is carried in a normal saline vehicle.

3. The method of claim 2 in which the TFPI is carried in said vehicle at a dose that does not affect the peripheral blood PT and APTT.

4. The method of claim 1 in which the TFPI is administered during microvascular reconstruction by free flap transfer.

5. The method of claim 1 in which the TFPI is administered during microvascular reconstruction by replantation.

*6. The method of claim 1 wherein said TFPI is a 277 amino protein having an alanine residue at its N-terminus.*

*7. A method for reducing thrombogenicity of vascular injury in a warm blooded mammal comprising administering topically to said mammal at the site of said vascular injury a thrombotic inhibitory effective amount of tissue factor pathway inhibitor (TFPI).*

*8. The method of claim 7 wherein said TFPI is a 277 amino acid protein having an alanine residue at its N-terminus.*

*9. The method of claim 8 wherein said vascular injury occurs during vascular reconstruction by free flap transfer.*

*10. The method of claim 8 wherein said vascular injury occurs during vascular reconstruction by replantation.*

*11. The method of claim 7 wherein said TFPI is a 276 amino acid protein.*

*12. The method of claim 7 in which said TFPI is carried in a saline vehicle.*

*13. The method of claim 12 in which said TFPI is carried in said vehicle at a dose that does not affect the peripheral blood PT and APTT.*

*14. The method of claim 7 wherein said vascular injury occurs during vascular reconstruction by free flat transfer.*

*15. The method of claim 7 wherein said vascular injury occurs during vascular reconstruction by replantation.*

*16. The method of claim 7 wherein said site of said vascular injury is a vein graft.*

*17. A method for reducing thrombogenicity of vascular anastomoses in a warm blooded mammal comprising administering topically to mammal at the site of vascular anastomoses contemporaneously with vascular reconstruction a thrombotic inhibitory effective amount of tissue factor pathway inhibitor (TFPI).*

*18. The method of claim 17 wherein said TFPI is a 277 amino acid protein having an alanine residue at its N-terminus.*

*19. The method of claim 17 wherein said TFPI is a 276 amino acid protein.*

*20. The method of claim 17 in which said TFPI is carried in a saline vehicle.*

*21. The method of claim 20 in which said TFPI is carried in said vehicle at a dose that does not affect the peripheral blood PT and APTT.*

*22. The method of claim 18 wherein said vascular anastomoses occurs during vascular reconstruction by free flap transfer.*

*23. The method of claim 18 wherein said vascular anastomoses occurs during vascular reconstruction by replantation.*

*24. The method of claim 17 wherein said vascular anastomoses occurs during vascular reconstruction by free flap transfer.*

*25. The method of claim 17 wherein said vascular anastomoses occurs during vascular reconstruction by replantation.*

*26. The method of claim 16 wherein said site of said vascular anastomoses is a vein graft.*

*27. A method for reducing thrombogenicity of a traumatized vessel surface in a warm blooded mammal comprising administering topically to said mammal at the site of said traumatized vessel surface a thrombotic inhibitory effective amount of tissue factor pathway inhibitor (TFPI).*

*28. The method of claim 27 wherein said TFPI is a 277 amino acid protein having an alanine residue at its N-terminus.*

*29. The method of claim 28 wherein said vessel surface is traumatized during vascular reconstruction by free flap transfer.*

*30. The method of claim 28 wherein said vessel surface is traumatized during vascular reconstruction by replantation.*

*31. The method of claim 27 wherein said TFPI is a 276 amino acid protein.*

*32. The method of claim 27 in which said TFPI is carried in a saline vehicle.*

*33. The method of claim 32 in which said TFPI is carried in said vehicle at a dose that does not affect the peripheral blood PT and APTT.*

*34. The method of claim 27 wherein said vessel surface is traumatized during vascular reconstruction by free flap transfer.*

*35. The method of claim 27 wherein said vessel surface is traumatized during vascular reconstruction by replantation.*

*36. The method of claim 27 wherein said traumatized vessel surface is a vein graft.*

* * * * *

UNITED STATES PATENT AND TRADEMARK OFFICE

CERTIFICATE OF CORRECTION

PATENT NO.: Re. 36,476

DATED: December 28, 1999

INVENTORS: Roger K. KHOURI, *et al.*

It is certified that errors appear in the above-identified patent and that said Letters Patent is hereby corrected as shown below:

In Claim 14, column 6, line 67, delete "flat" and insert --flap--.

In Claim 17, column 7, line 7, after "to" insert --said--.

In Claim 26, column 8, delete "16" and insert --17--.

Signed and Sealed this

Twelfth Day of September, 2000

*Attest:*

Q. TODD DICKINSON

*Attesting Officer*

*Director of Patents and Trademarks*